(12) United States Patent
Paulicka et al.

(10) Patent No.: US 12,332,234 B2
(45) Date of Patent: Jun. 17, 2025

(54) SOLUTION COLLECTION DEVICE WITH EVALUATION ELEMENT

(71) Applicant: Siemens Healthcare Diagnostics Inc., Tarrytown, NY (US)

(72) Inventors: Peter Paulicka, Röttenbach (DE); Jennifer Samproni, Braintree, MA (US); Manish Deshpande, Newton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 377 days.

(21) Appl. No.: 17/299,816

(22) PCT Filed: Dec. 5, 2019

(86) PCT No.: PCT/US2019/064623
§ 371 (c)(1),
(2) Date: Jun. 4, 2021

(87) PCT Pub. No.: WO2020/118018
PCT Pub. Date: Jun. 11, 2020

(65) Prior Publication Data
US 2022/0018827 A1     Jan. 20, 2022

Related U.S. Application Data

(60) Provisional application No. 62/776,825, filed on Dec. 7, 2018.

(51) Int. Cl.
*G01N 33/49* (2006.01)
*B01L 3/00* (2006.01)
(Continued)

(52) U.S. Cl.
CPC ............ *G01N 33/491* (2013.01); *B01L 3/508* (2013.01); *G01N 21/251* (2013.01); *G01N 21/77* (2013.01);
(Continued)

(58) Field of Classification Search
None
See application file for complete search history.

(56) References Cited

U.S. PATENT DOCUMENTS

| 484,487 A | 10/1892 | Wunderlich |
| 3,954,623 A | 5/1976 | Hammer et al. |

(Continued)

FOREIGN PATENT DOCUMENTS

| CN | 2240724 Y | 11/1996 |
| EP | 0597268 A1 | 5/1994 |

(Continued)

OTHER PUBLICATIONS

International Search Report and Written Opinion of International Application No. PCT/US2019/064623 dated Feb. 13, 2020.
(Continued)

*Primary Examiner* — Tarifur R Chowdhury
*Assistant Examiner* — Roberto Fabian, Jr.

(57) ABSTRACT

A blood testing device for detecting hemolysis in a blood sample is described. The blood testing device comprises an housing for containing the blood sample. The housing has a treatment window and an optical zone formed therein. The blood testing device further includes an acoustic transducer positioned to selectively generate acoustic forces directed into the treatment window of the housing and a control unit for selectively actuating and deactuating the acoustic transducer to permit colorimetric analysis of plasma within the blood sample.

20 Claims, 7 Drawing Sheets

(51) Int. Cl.
  *G01N 21/25* (2006.01)
  *G01N 21/77* (2006.01)
(52) U.S. Cl.
  CPC ..... *G01N 33/4915* (2013.01); *G01N 33/4925* (2013.01); *B01L 2200/0689* (2013.01); *B01L 2200/16* (2013.01); *B01L 2300/0663* (2013.01); *B01L 2300/0681* (2013.01); *B01L 2400/0478* (2013.01); *G01N 2021/7763* (2013.01); *G01N 2201/0221* (2013.01)

(56) References Cited

U.S. PATENT DOCUMENTS

| | | | |
|---|---|---|---|
| 4,844,871 | A | 7/1989 | Polaschegg |
| 5,125,415 | A | 6/1992 | Bell |
| 5,330,420 | A | 7/1994 | Lee |
| 5,876,605 | A | 3/1999 | Kitajima et al. |
| 5,979,669 | A | 11/1999 | Kitajima et al. |
| 5,996,811 | A | 12/1999 | Kitajima et al. |
| 6,045,699 | A | 4/2000 | Yazawa et al. |
| 6,196,998 | B1 | 3/2001 | Jansen et al. |
| 6,217,540 | B1 | 4/2001 | Kitajima et al. |
| 6,220,453 | B1 | 4/2001 | Kitajima et al. |
| 6,225,130 | B1 | 5/2001 | Kitajima et al. |
| 6,280,621 | B1 | 8/2001 | Yazawa et al. |
| 6,328,167 | B1 | 12/2001 | Seshimoto et al. |
| 6,375,856 | B1 | 4/2002 | Seshimoto et al. |
| 6,383,818 | B1 | 5/2002 | Arai et al. |
| 6,387,290 | B1 | 5/2002 | Brody et al. |
| 6,405,876 | B1 | 6/2002 | Seshimoto et al. |
| 6,659,288 | B2 | 12/2003 | Amano et al. |
| 6,659,975 | B2 | 12/2003 | Amano et al. |
| 6,936,473 | B2 | 8/2005 | Nanba et al. |
| RE39,457 | E | 1/2007 | Guirguis |
| 7,323,144 | B2 | 1/2008 | Arai et al. |
| 7,407,578 | B2 | 8/2008 | Sakaino et al. |
| 7,500,569 | B2 | 3/2009 | Manoussakis et al. |
| 7,896,818 | B2 | 3/2011 | Fremming et al. |
| 7,927,810 | B2 | 4/2011 | Togawa et al. |
| 8,057,672 | B2 | 11/2011 | Chung et al. |
| 8,444,621 | B2 | 5/2013 | Fremming et al. |
| 8,535,617 | B2 | 9/2013 | MacDonald et al. |
| 8,574,497 | B2 | 11/2013 | Pfaff |
| 8,846,333 | B2 | 9/2014 | Karlsson |
| 8,865,003 | B2 * | 10/2014 | Yang ................. B01L 3/502776 250/281 |
| 8,999,268 | B2 | 4/2015 | Egger-Cimenti et al. |
| 9,028,688 | B2 | 5/2015 | Okamoto et al. |
| 9,261,494 | B2 | 2/2016 | Choi et al. |
| 9,283,313 | B2 | 3/2016 | Huemer |
| 9,322,761 | B2 | 4/2016 | Miller |
| 9,427,707 | B2 | 8/2016 | Montagu et al. |
| 9,517,026 | B2 | 12/2016 | Gelfand et al. |
| 9,597,028 | B2 * | 3/2017 | Marchiarullo ... A61B 5/150343 |
| 9,757,095 | B2 | 9/2017 | Terbrueggen et al. |
| 9,816,979 | B2 | 11/2017 | Kelso et al. |
| 9,983,199 | B2 | 5/2018 | Karlsson |
| 9,993,816 | B2 | 6/2018 | Biesbrouck |
| 10,111,610 | B2 | 10/2018 | Tan et al. |
| 2001/0039057 | A1 | 11/2001 | Douglas et al. |
| 2002/0036170 | A1 | 3/2002 | Harvey et al. |
| 2003/0185707 | A1 | 10/2003 | Iwaki et al. |
| 2004/0035792 | A1 | 2/2004 | Rauch et al. |
| 2005/0227370 | A1 | 10/2005 | Ramel et al. |
| 2006/0016747 | A1 | 1/2006 | Sakaino et al. |
| 2008/0003141 | A1 | 1/2008 | Iketani |
| 2008/0017577 | A1 | 1/2008 | Yi et al. |
| 2010/0111763 | A1 | 5/2010 | Kahn et al. |
| 2011/0076697 | A1 | 3/2011 | Ruvinsky et al. |
| 2012/0086938 | A1 | 4/2012 | Folkenberg |
| 2012/0232803 | A1 | 9/2012 | Viola et al. |
| 2013/0040333 | A1 | 2/2013 | Karlsson |
| 2013/0184188 | A1 | 7/2013 | Ewart et al. |
| 2014/0305196 | A1 | 10/2014 | Ellis et al. |
| 2014/0329268 | A1 | 11/2014 | Karlsson |
| 2015/0090674 | A1 | 4/2015 | Lee et al. |
| 2015/0153323 | A1 | 6/2015 | Huemer |
| 2016/0074569 | A1 | 3/2016 | Schuetz et al. |
| 2016/0096148 | A1 | 4/2016 | Schuetz et al. |
| 2016/0106353 | A1 | 4/2016 | Schuetz et al. |
| 2016/0106907 | A1 | 4/2016 | Winkler et al. |
| 2016/0202237 | A1 * | 7/2016 | Zeng ................. G01N 1/4077 435/287.1 |
| 2016/0258937 | A1 | 9/2016 | Ellington et al. |
| 2016/0258945 | A1 | 9/2016 | Malima et al. |
| 2016/0313298 | A1 | 10/2016 | Wright et al. |
| 2017/0059550 | A1 | 3/2017 | Bokka Srinivasa Rao et al. |
| 2017/0095190 | A1 | 4/2017 | Sloan et al. |
| 2017/0108516 | A1 | 4/2017 | Ledden et al. |
| 2017/0241977 | A1 | 8/2017 | Wilson et al. |
| 2017/0248618 | A1 | 8/2017 | Baxter et al. |
| 2017/0252706 | A1 | 9/2017 | Xu et al. |
| 2017/0299481 | A1 | 10/2017 | Laugham, Jr. |
| 2017/0328896 | A1 * | 11/2017 | Luloh ................. G01N 33/558 |
| 2017/0354362 | A1 * | 12/2017 | Xu ................. A61B 5/150251 |
| 2018/0125464 | A1 | 5/2018 | Kolb et al. |
| 2018/0128807 | A1 | 5/2018 | Ishizaka et al. |
| 2018/0128844 | A1 | 5/2018 | Shizaka et al. |
| 2018/0136194 | A1 | 5/2018 | Sinn Blandy et al. |
| 2018/0143116 | A1 | 5/2018 | Urano et al. |
| 2018/0230508 | A1 | 8/2018 | Idelevich et al. |
| 2018/0304261 | A1 | 10/2018 | Ho et al. |
| 2018/0321228 | A1 | 11/2018 | Cooper et al. |
| 2019/0046715 | A1 | 2/2019 | Margraf et al. |
| 2019/0072539 | A1 | 3/2019 | Eriksson et al. |

FOREIGN PATENT DOCUMENTS

| | | |
|---|---|---|
| JP | 2015503104 A | 1/2015 |
| JP | 2015530566 A | 10/2015 |
| WO | 2007000986 A1 | 1/2007 |
| WO | 2009110089 A1 | 9/2009 |
| WO | 2010113355 A1 | 7/2010 |
| WO | 2011033000 A2 | 3/2011 |
| WO | 2014019254 A1 | 2/2014 |
| WO | 2014172234 A1 | 10/2014 |
| WO | 2014207140 A1 | 12/2014 |
| WO | 2014207150 A1 | 12/2014 |
| WO | 2015191450 A1 | 12/2015 |
| WO | WO-2018065626 A1 * | 4/2018 ........ B01L 3/502761 |
| WO | 2018226994 A1 | 12/2018 |
| WO | 2019025914 A1 | 2/2019 |
| WO | 2020118021 A1 | 6/2020 |
| WO | 2020185272 A1 | 9/2020 |
| WO | 2021015808 A1 | 1/2021 |

OTHER PUBLICATIONS

Liu et al., "Membrane-based, sedimentation-assisted plasma separator for point-of-care applications", Nov. 5, 2013, Anal Chem. 85(21), pp. 1-17.
Adiga et al., "Hemolytic index—A tool to measure hemolysis in vitro", 2016, IOSR Journal of Biotechnology and Biochemistry, vol. 2, Issue 2, pp. 49-52.
McCaughey et al., "Current Methods of Haemolysis Detection and Reporting as a Source of Risk to Patient Safety: a Narrative Review", 2016, Clin Biochem Rev 37 (4), pp. 143-151.
Peter J. Howanitz MD, Presentation on Hemolysis, <https://www.slideserve.com/altessa/peter-j-howanitz-md>, Jul. 20, 2014, pp. 1-30.
Zhou et al., "Optofluidic Sensor for Inline Hemolysis Detection on Whole Blood", Feb. 2018, ACS Sensors, 3, pp. 784-791.

* cited by examiner

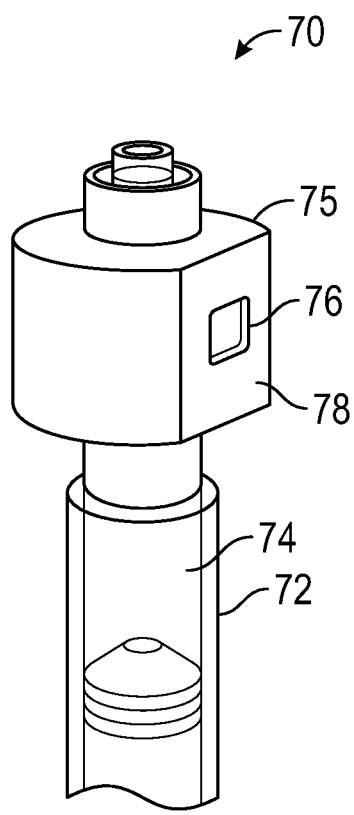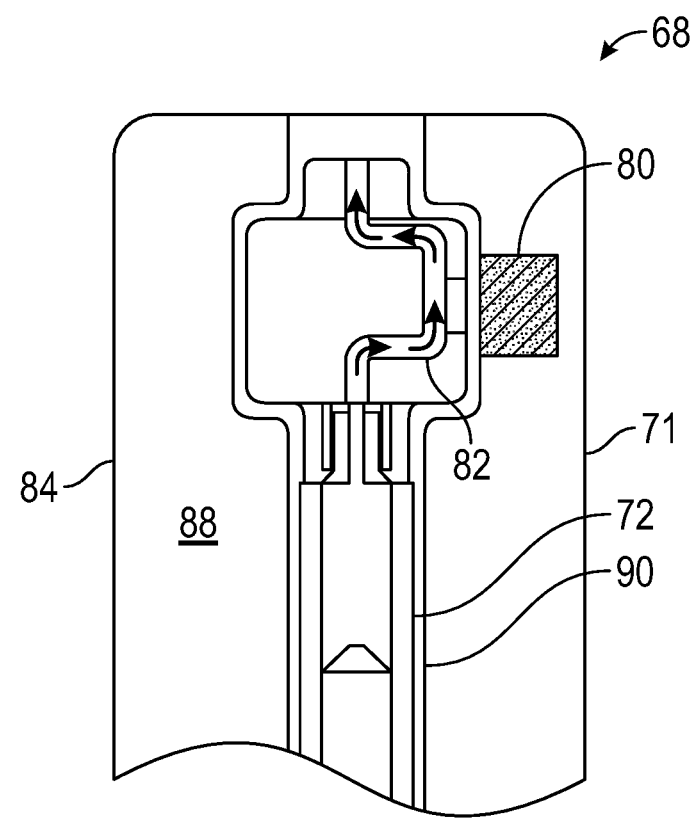
FIG. 4A        FIG. 4B
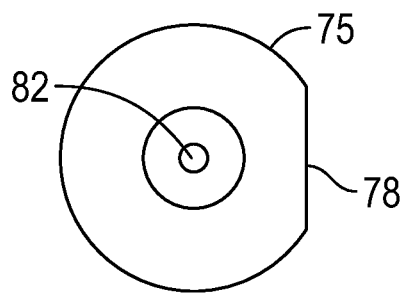
FIG. 4C

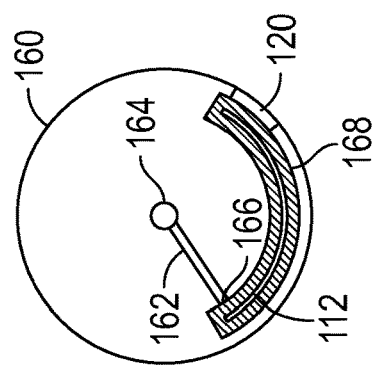
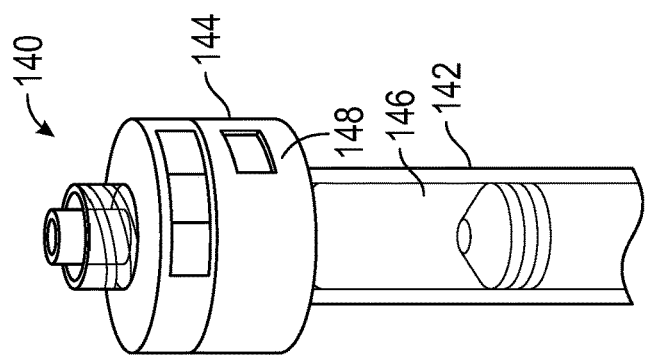
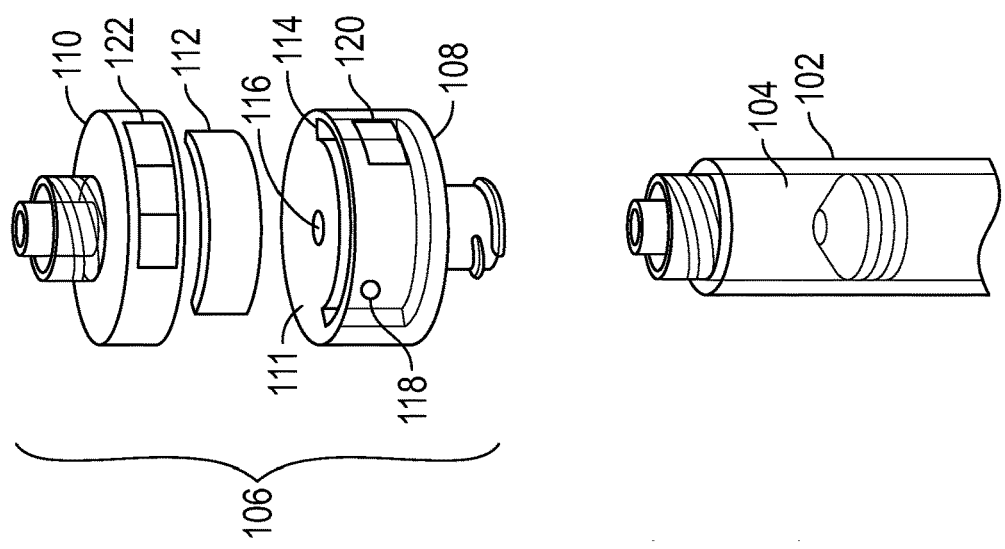

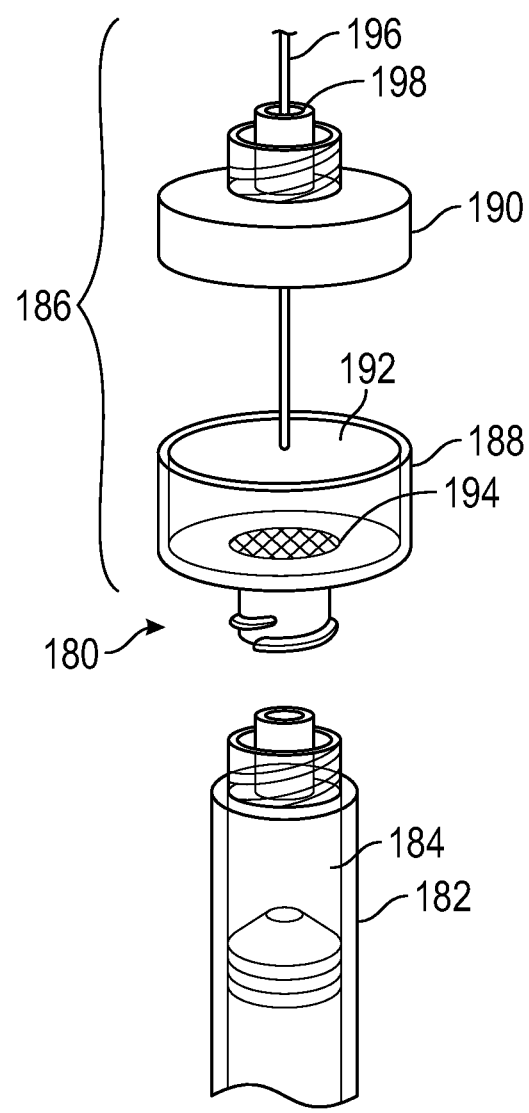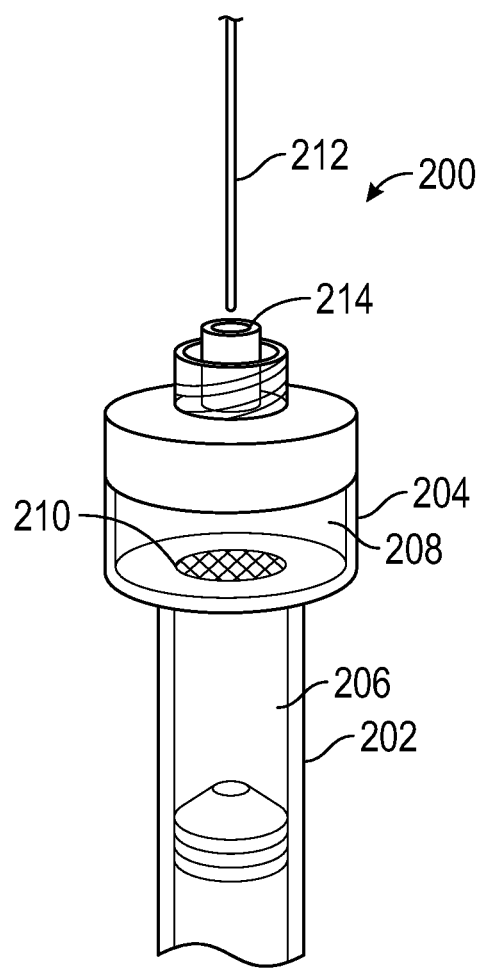
FIG. 9
FIG. 10

SOLUTION COLLECTION DEVICE WITH EVALUATION ELEMENT

The subject application claims benefit under 35 USC § 119(e) of U.S. provisional Application No. 62/776,825, filed Dec. 7, 2018. The entire contents of the above-referenced patent application are hereby expressly incorporated herein by reference.

STATEMENT REGARDING FEDERALLY SPONSORED RESEARCH AND DEVELOPMENT

Not Applicable.

BACKGROUND

Point-of-care testing refers generally to medical testing at or near the site of patient care, such as in an emergency room. A desired outcome of such tests is often rapid and accurate lab results to determine a next course of action in the patient care. A number of such point of care tests involve analysis of a blood sample from the patient. The ideal blood sample is pure plasma separated from the source whole blood sample. However, even in such plasma samples, there are often residual broken blood cells as a result of hemolysis due to imperfections in obtaining the sample from the subject, pre-analytical blood sample handling, and the whole blood separation process. In certain cases, these hemolysed cells can interfere with the integrity of analytical test results.

For example, if hemolysis occurs, resulting free hemoglobin in the sample may cause interference in a number of tests, thereby leading to a signal reduction, reduced measurement accuracy and precision, or to false positive results at the other end of the spectrum. For one, it has been found that the potassium concentration in a corresponding sample may increase significantly and cause a high risk of misdiagnosis in a diagnostic test for potassium levels.

To determine whether hemolysis has occurred, a number of tests have been developed to determine hemoglobin (Hb) levels in a blood sample. One common reagent used for determining Hb levels or hemolysis in a blood sample is referred to as Drabkin's Reagent. Drabkin's Reagent comprises a mixture that works by lysing red blood cells and quantitatively converting all Hb in a sample into one form, cyanomethaemoglobin, which is then be measured on a spectrometer using a single wavelength. As such, Drabkin's Reagent measures intracellular hemoglobin as well as free hemoglobin. For at least this reason, Drabkin's Reagent does not provide a realistic picture of the extent of free Hb present at a particular point in time in a sample, which is indicative of hemolysis.

A need exists, therefore, for rapid, point-of-care testing of a blood sample to determine whether hemolysis has occurred that overcomes the shortcomings of the present testing regimes.

BRIEF DESCRIPTION OF THE DRAWINGS

The accompanying drawings, which are incorporated in and constitute a part of this specification, illustrate one or more implementations described herein and, together with the description, explain these implementations. In the drawings:

FIGS. 4A-4C illustrate views of portions of another version of a fluid collection device constructed in accordance with the present disclosure.

FIG. 6 illustrates an exploded, perspective view of a blood testing device removably attachable to a fluid housing such as a syringe constructed in accordance with one embodiment of the present disclosure.

FIG. 7 illustrates a perspective view of another version of a blood testing device constructed in accordance with one embodiment of the present disclosure.

FIG. 8 illustrates top plan view of a blood testing device constructed in accordance with one embodiment of the present disclosure.

FIG. 9 illustrates an exploded, perspective view of a blood testing device removably attachable to a fluid housing such as a syringe constructed in accordance with one embodiment of the present disclosure.

FIG. 10 illustrates a perspective view of another version of a blood testing device constructed in accordance with one embodiment of the present disclosure.

DETAILED DESCRIPTION

Figure 1:
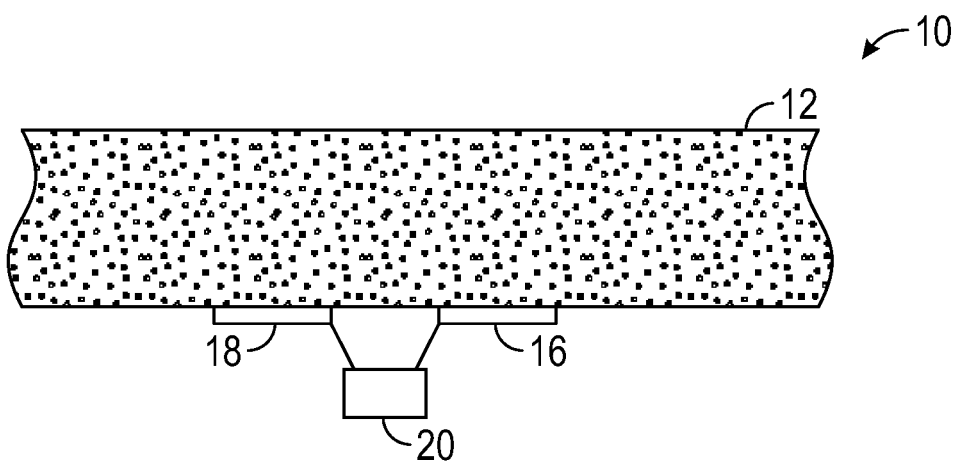
FIG. 1 is a cross sectional view of a portion of a blood testing device constructed in accordance with one embodiment of the present disclosure containing a blood sample.
Figure 2:
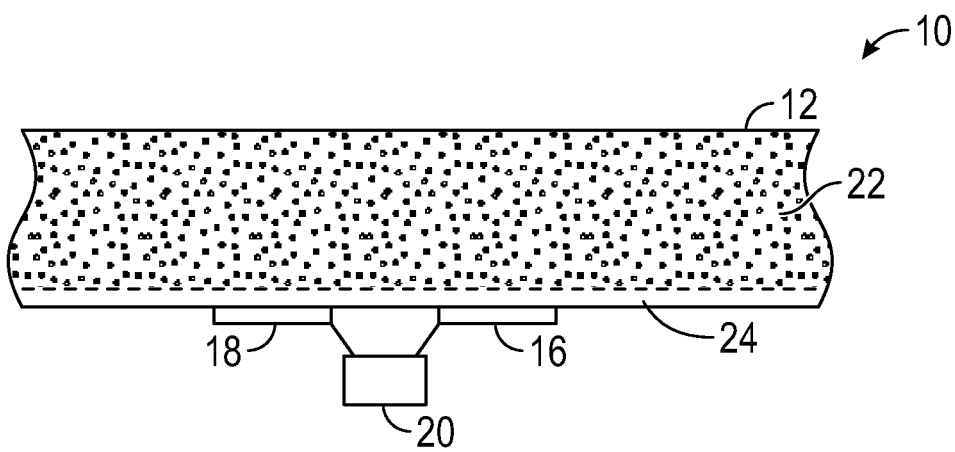
FIG. 2 is a cross sectional view of a portion of the blood testing device of FIG. 1 showing a sample of acoustically treated blood in accordance with one embodiment of the present disclosure in which blood cells and plasma within a blood sample are separated into a first zone containing plasma and blood cells, and a second zone containing plasma and being substantially devoid of blood cells.

The following detailed description refers to the accompanying drawings. The same reference numbers in different drawings may identify the same or similar elements.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Circuitry, as used herein, may be analog and/or digital, components, or one or more suitably programmed microprocessors and associated hardware and software, or hardwired logic. Also, "components" may perform one or more functions. The term "component," may include hardware, such as a processor, an application specific integrated circuit (ASIC), or a field programmable gate array (FPGA), or a combination of hardware and software. Software includes one or more computer executable instructions that when executed by one or more component cause the component to perform a specified function. It should be understood that the algorithms described herein are stored on one or more non-transitory memory. Exemplary non-transitory memory includes random access memory, read only memory, flash memory or the like. Such non-transitory memory may be electrically based or optically based.

As used herein, the term "substantially" means that the subsequently described parameter, event, or circumstance completely occurs or that the subsequently described parameter, event, or circumstance occurs to a great extent or degree. For example, the term "substantially" means that the subsequently described parameter, event, or circumstance occurs at least 90% of the time, or at least 91%, or at least 92%, or at least 93%, or at least 94%, or at least 95%, or at least 96%, or at least 97%, or at least 98%, or at least 99%, of the time, or means that the dimension or measurement is within at least 90%, or at least 91%, or at least 92%, or at least 93%, or at least 94%, or at least 95%, or at least 96%, or at least 97%, or at least 98%, or at least 99%, of the referenced dimension or measurement.

In accordance with one aspect, there are provided devices, systems, and processes for determining a presence of hemolysis in a sample. Advantageously, devices, systems, and processes described herein determine whether hemolysis has occurred in a sample based upon a colorimetry assessment of a portion of the sample.

In accordance with another aspect, there are provided devices, systems, and processes for a blood collection container having a hemolysis indicating feature.

In accordance with another aspect, there are provided blood collection devices, systems, accessories and processes having a plasma separating feature.

In accordance with another aspect, there are provided blood collection devices, systems, accessories, and processes having a hemolysis indicating feature.

Referring now to the Figures and in particular to FIG. 1, shown therein is a diagramatic view of a blood testing device 10 constructed in accordance with the present disclosure. In general, the blood testing device 10 includes a housing 12, an acoustic transducer 16, a reader 18, and a control unit 20 connected to the transducer 16 and the reader 18. The housing 12 is constructed of a fluid impermeable material so that the housing 12 can hold and contain a sample of blood containing blood cells, suspended within plasma. The housing 12 can be a syringe or a vacutainer, for example that can be used for collecting blood and transporting the blood for purposes of testing. The blood may be collected from an animal, such as a human, or a non-human (such as a cat, dog, cow, horse, fish, or the like). The acoustic transducer 16, the reader 18, and the control unit 20 may be located outside of the housing 12 as shown in FIG. 1 or inside the housing 12 (not shown). The acoustic transducer 16 selectively generates acoustic forces that are directed to the housing 12. In some embodiments, the acoustic transducer 16 can be tuned so as to provide a magnitude and/or frequency of acoustic forces so as to facilitate separation of the undamaged blood cells from the plasma and damaged blood cells. The magnitude and/or frequency of the acoustic forces generated by the acoustic transducer 16 can be selected depending upon a size and/or construction of the housing 12, or composition of the blood sample within the housing 12. In one embodiment, the acoustic transducer 16 can be a piezoelectric element. At least a portion of the housing 12, adjacent to the transducer 16, is constructed of a material that functions to pass the acoustic forces generated by the acoustic transducer 16 into the sample contained within the housing 12. Exemplary materials that can be used to form the housing 12 include glass, crystal, and the like. Parts of the housing 12 away from the transducer 16 can be made of other materials such as plastic. The application of the acoustic forces into the sample by the acoustic transducer 16 causes the blood cells within the blood to move within the plasma to form a first zone 22 having an increased density or concentration of the blood cells than the blood contained prior to the application of the acoustic forces, and at least one second zone 24 being substantially only plasma, i.e., substantially devoid of any undamaged blood cells. The reader 18 is positioned adjacent to the second zone 24 and functions to read at least one parameter of the plasma. In one embodiment, the reader 18 is an optical reader, such as a camera or photospectrometer having a field of view overlapping with the housing 12 such that the plasma within the second zone is visible to the reader 18. The optical reader 18 is positioned such that the second zone 24 is within the field of view. The control unit 20 selectively actuates/deactuates the acoustic transducer 16 to cause separation of the blood cells and plasma into the first zone 22 and the second zone 24. Then, in some embodiments, the control unit 20 actuates the reader 18 to capture information indicative of at least one parameter of the plasma. The information captured by the reader 18 is then transferred to the control unit 20 to determine a degree of hemolysis within the sample of blood. The control unit 20 can be constructed of circuitry and/or a combination of circuitry and software.

When the reader 18 is the optical reader, the degree of hemolysis can be determined by the control unit 20 based upon a colorimetric analysis of the sample. That is, when the sample is devoid of hemolysis and is illuminated with white light, the plasma will be substantially devoid of any color, i.e., the sample will be transparent. When hemolysis has occurred within the sample, the plasma will be pink when the plasma is illuminated with white light. By correlating the color of the plasma with predetermined colors indicative of an extent of hemolysis occurring within other samples, the extent of hemolysis within the sample can be determined. Depending upon a color of a backdrop, and/or color of illumination of the plasma, colors detected by the reader 18 indicative of an extent of hemolysis may differ.

Information indicative of an extent of hemolysis within the sample can be used to determine whether the blood has hemolysis.

Figure 3:
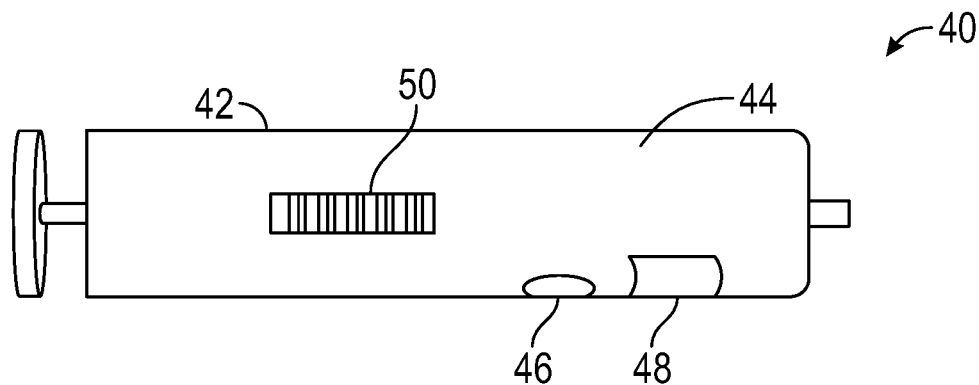
FIG. 3 is an orthogonal view of a fluid collection device having an integrated blood testing device constructed in accordance with the present disclosure.

FIG. 3 illustrates a blood testing device 40 constructed in accordance with one embodiment of the present disclosure. The blood testing device 40 is provided with a fluid container such as a syringe 42 or vacutainer having a fluid reservoir 44 for containing blood. The blood testing device 40 may also be provided with an acoustic transducer 46, an optical zone 48, and a bar code 50 which identifies the contents of the syringe 42 and can be correlated to specific patients. The acoustic transducer 46 may be provided with any suitable shape, such as planar, arcuate, or the like. In some embodiments, the acoustic transducer 46 may be provided with a shape to match a shape of the optical zone 48, or other section of the blood testing device 40 to be stimulated by the acoustic transducer 46. In such an embodiment, the blood testing device 40 allows the blood to be acoustically treated using the acoustic transducer 46 after which the blood may be analyzed using an optical reader or the human eye through the optical zone 48. Once a degree of hemolysis within the sample of blood has been determined, a decision can be made whether or not to continue with further testing of the sample of blood.

Referring now to FIGS. 4A-4C, shown therein is an embodiment of a blood testing device 70 and reader 71. The blood testing device 70 has a fluid housing 72, a fluid reservoir 74, a fluid treatment area 75, an optical zone 76, a treatment window 78, and a flow port 82. The reader 71 has a reading device 80, a flow path 82, and an analysis unit 84. In this embodiment of the blood testing device 70, a blood sample is contained in the fluid housing 72 and directed along the flow path 82 into the fluid treatment area 75 where the blood sample is directed to flow past the treatment window 78. The treatment window 78 is constructed of a material that functions to pass acoustic forces generated by an acoustic transducer into the blood sample contained within the fluid housing 72.

The reading device 80 is part of the analysis unit 84 and is provided with an acoustic transducer (not shown) and an optical reader (not shown) which operate as described above to acoustically treat the blood sample. The acoustic transducer may be provided with a planar shape so as to mate with the treatment window 78 of the blood testing device 70. The optical reader of the reading device 80 has a field of view directed to the optical zone 76 where the acoustically treated blood sample may be read. The analysis unit 84 actuates the acoustic transducer to acoustically treat the blood sample and move the blood cells away from the optical zone 76 such that only the plasma is visible in the optical zone 76. Then the optical reader captures an image of the plasma and any backdrop and sends the image to the analysis unit 84 for colorimetric analysis as discussed above. The analysis unit 84 may be provided with further blood analysis features (not shown) such as blood gas analysis which may further analyze the blood sample after it passes through the flow path 82. The reader 71 may be portable and have a housing 88 that includes a slot 90 sized and dimensioned to receive the blood testing device 70 such that the optical zone 76 is in the field of view of the optical reader and the treatment window overlaps with the acoustic transducer. The housing 88 can be provided in a variety of shapes such as in a shape of a hot dog bun, for instance. The analysis unit 84 can be supported in the housing 88 or be separate therefrom. For example, the reading device 80 can be provided with a wireless transceiver to communicate with the analysis unit 84. The analysis unit 84 may be constructed and function in a similar manner as the control unit 20 discussed above.

Figure 5B:
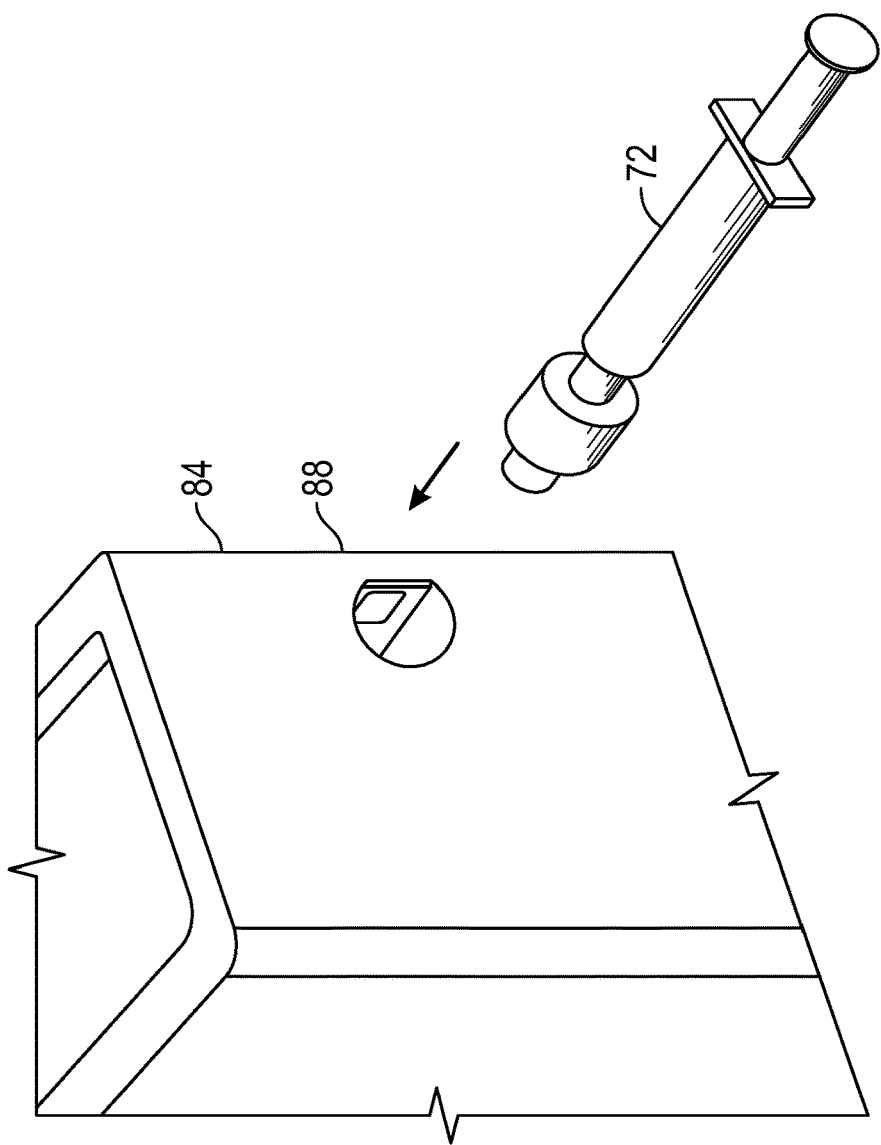
FIG. 5B illustrates the fluid housing of FIG. 4 being inserted into a port of another version of a reader for acoustic treatment and colorimetric analysis in accordance with one embodiment of the present disclosure.
Figure 5A:
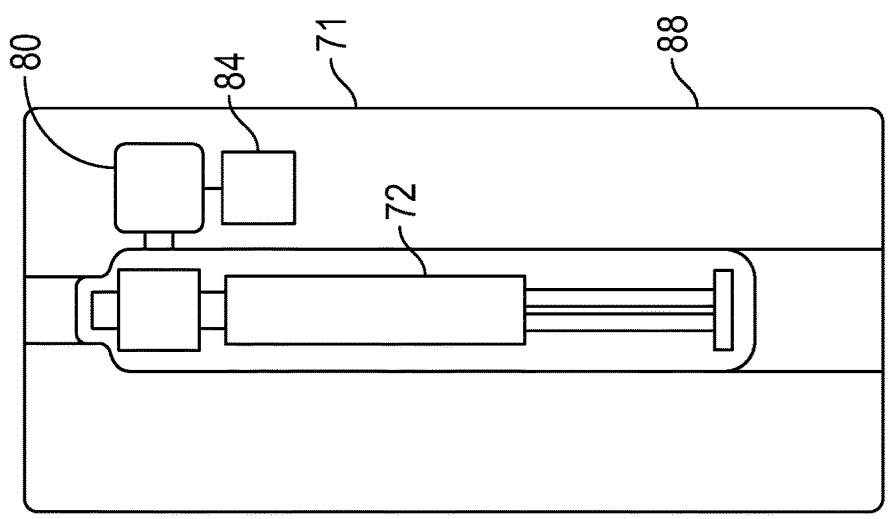
FIG. 5A illustrates a fluid housing of FIG. 4 being inserted into a slot of a reader for acoustic treatment and colorimetric analysis in accordance with one embodiment of the present disclosure.

FIG. 5 illustrates another variation of the reader 71 in which the fluid housing 72 of FIG. 4 may be inserted into the housing 88 so that the blood sample may be acoustically treated and read by the reading device 80 as described above.

Referring now to FIG. 6, a lateral flow blood testing device 100 constructed in accordance with the present disclosure is shown having a fluid housing 102, a first fluid reservoir 104, and a fluid treatment module 106. The fluid treatment module 106 of the lateral flow blood testing device 100 is provided with a lower portion 108, an upper portion 110, a second fluid reservoir 111, a lateral flow strip 112, a fluid channel 114, a first fluid port 116, a second fluid port 118, an optical zone 120, and a bar code 122.

The lower portion 108 and the upper portion 110 of the fluid treatment module 106 are sealably connected to form the second fluid reservoir 111. When the fluid treatment module 106 is connected to the fluid housing 102, a blood sample may be transferred from the first fluid reservoir 104 to the second fluid reservoir 111. Once in the second fluid reservoir 111, a portion of the blood sample may be directed through the second fluid port 118 into the fluid channel 114 where the blood sample passes through the lateral flow strip 112. Through capillary action (which may also be referred to as capillary flow), the lateral flow strip 112 causes the separation of undamaged blood cells and plasma in the blood sample as described more fully in U.S. patent application Ser. No. 15/317,748, the entirety of which is incorporated herein by reference. The plasma that has passed through the lateral flow strip 112 may then be analyzed in the optical zone 120 to determine a degree of hemolysis using an optical reader as described above or human eyes.

To facilitate directing the blood sample into the second fluid port 118, the first fluid port 116 may be temporarily sealed using a removable cap (not shown), for instance, that temporarily prevents movement of the blood sample through the first fluid port 116. When the blood sample has been analyzed using the lateral flow blood testing device 100, the cap may be removed and the blood sample may be allowed to pass through the first fluid port 116 to be used for further testing, for instance, as desired.

As described above, the bar code 122 may be used to identify the blood sample, the patient the blood sample belongs too, the test to be performed, and the like.

FIG. 7 illustrates a lateral flow blood testing device 140 having a fluid housing 142, a fluid treatment module 144, a first fluid reservoir 146, and a second fluid reservoir 148. The lateral flow blood testing device 140 is similar to the lateral flow blood testing device 100 described above, therefore, in the interest of brevity only the differences will be described herein. In the embodiment shown in FIG. 7, the fluid treatment module 144 and the fluid housing 142 are integrated to form the lateral flow blood testing device 140.

FIG. 8 illustrates a top plan view of a fluid treatment module 160 similar to fluid treatment modules 106 and 144. In this embodiment, the fluid treatment module 160 is provided with a fluid channel 162 that connects a first fluid port 164 with a second fluid port 166 to direct a flow of a blood sample into a fluid channel 168 for separation of the blood sample into at least two constituent parts as described above. The fluid channel 168 houses the lateral flow strip 112 that functions to separate the undamaged blood cells from the plasma so that the plasma and any color caused by damaged blood cells is visible in the optical zone 120.

Referring now to FIG. 9, shown therein is another embodiment of a lateral flow blood testing device 180 having a fluid housing 182, a fluid reservoir 184, and a fluid treatment module 186. The fluid treatment module 186 of the lateral flow blood testing device 180 is provided with a lower portion 188, an upper portion 190, a second fluid reservoir 192, and a lateral flow membrane 194.

The lower portion 188 and the upper portion 190 of the fluid treatment module 186 are sealably connected to form the second fluid reservoir 192. When the fluid treatment module 186 is connected to the fluid housing 182, a blood sample may be transferred from the first fluid reservoir 184 to the second fluid reservoir 192. As the blood sample is transferred from the first fluid reservoir 184 to the second fluid reservoir 192 the blood sample passes through the lateral flow membrane 194 and the blood sample is separated into at least two constituent parts, i.e., undamaged blood cells remain in the first fluid reservoir 184 and plasma with any damaged blood cells pass through the lateral flow membrane 194 and into the second fluid reservoir 192.

At least the lower portion 188 of the fluid treatment module 186 is constructed of an optically clear material which allows the plasma that has passed through the lateral flow membrane 194 to be colorimetrically analyzed in the second fluid reservoir 192 using an optical reader as described above or human eyes.

Also shown in FIG. 9 is a probe 196 which may be attached to or part of a blood analysis machine (not shown) such as a blood gas analyzer. Where whole blood is needed for analysis, the probe 196 may be passed through a fluid port 198 in the fluid treatment module 186, through the second fluid reservoir 192, and through the lateral flow membrane 194 into the first fluid reservoir 184 where the blood sample has not been separated.

FIG. 10 illustrates another version of a lateral flow blood testing device 200 having a fluid housing 202, a fluid treatment module 204, a first fluid reservoir 206, a second fluid reservoir 208, a lateral flow membrane 210, and a fluid port 214. The lateral flow blood testing device 200 is similar to the lateral flow blood testing device 180 described above, therefore, in the interest of brevity only the differences will be described herein. In the embodiment shown in FIG. 10, the fluid treatment module 204 and the fluid housing 202 are integrated into a unitary structure, rather than removably connected to form the lateral flow blood testing device 200.

A probe 212 is also shown which may be attached to or part of a blood analysis machine (not shown) such as a blood gas analyzer. Where whole (unseparated) blood is needed for analysis, the probe 212 may be passed through the fluid port 214 in the fluid treatment module 204, through the second fluid reservoir 206, and through the lateral flow membrane 210 into the first fluid reservoir 206 where the blood sample has not been separated.

Figure 13:
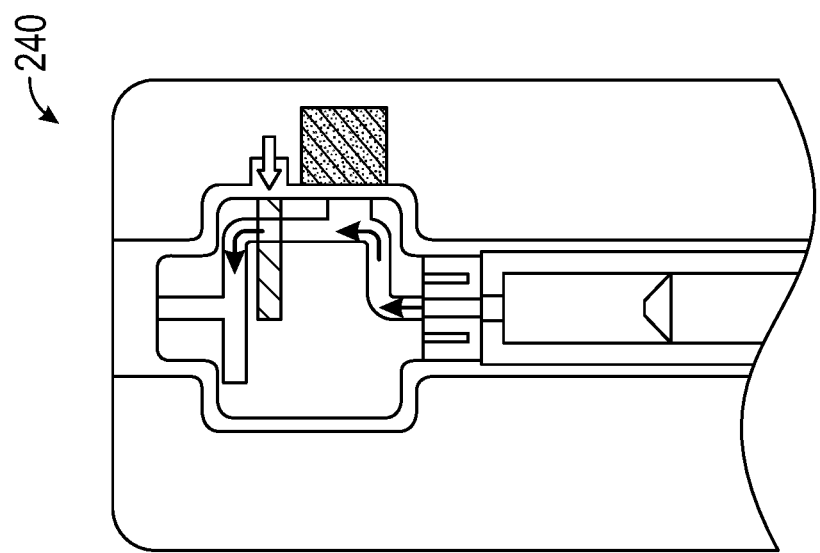
FIG. 13 illustrates another cross-sectional view of the blood testing device of FIG. 11 having the closeable gate in a second position, and positioned within the slot of the reader in accordance with the present disclosure.
Figure 12:
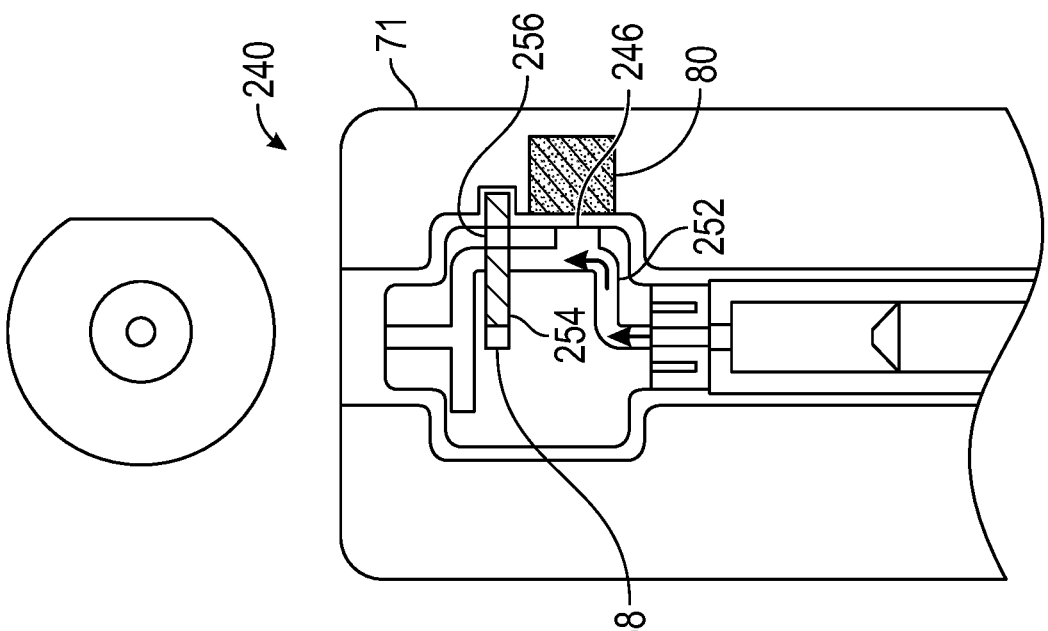
FIG. 12 illustrates a cross-sectional view of the blood testing device of FIG. 11 having the closeable gate in a first position, and positioned within a slot of a reader in accordance with the present disclosure.
Figure 11:
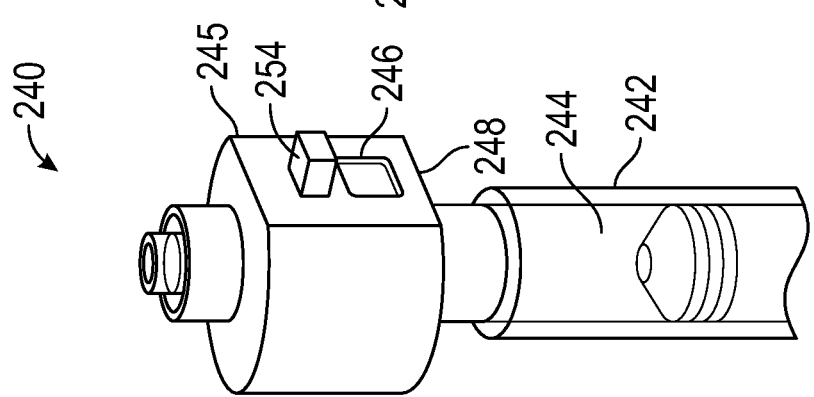
FIG. 11 illustrates a perspective view of a blood testing device having a closeable gate constructed in accordance with one embodiment of the present disclosure.

Referring now to FIGS. 11-13, shown therein is yet another version of a blood testing device 240 similar to the blood testing device 70 shown in FIG. 4 that can be read by the reader 71. In the interest of brevity, only the differences will be described in detail herein. The blood testing device 240 is provided with a fluid housing 242 a fluid reservoir 244, a fluid treatment area 245, an optical zone 246, a treatment window 248, a flow path 252, a gate 254 having a port 256, and a gate guide channel 258.

When the gate 254 is in a first position (shown in FIG. 12), the flow path 252 is restricted such that a blood sample in the flow path 252 stops in the optical zone 246 where the sample may be acoustically treated to move undamaged blood cells away from the plasma adjacent to the optical zone 246 and read with the reader 71 as described above.

Once the blood sample has been analyzed the gate 254 may be moved to a second position (shown in FIG. 13), which moves the port 256 into the flow path 252 allowing the blood sample to pass.

Figure 16:
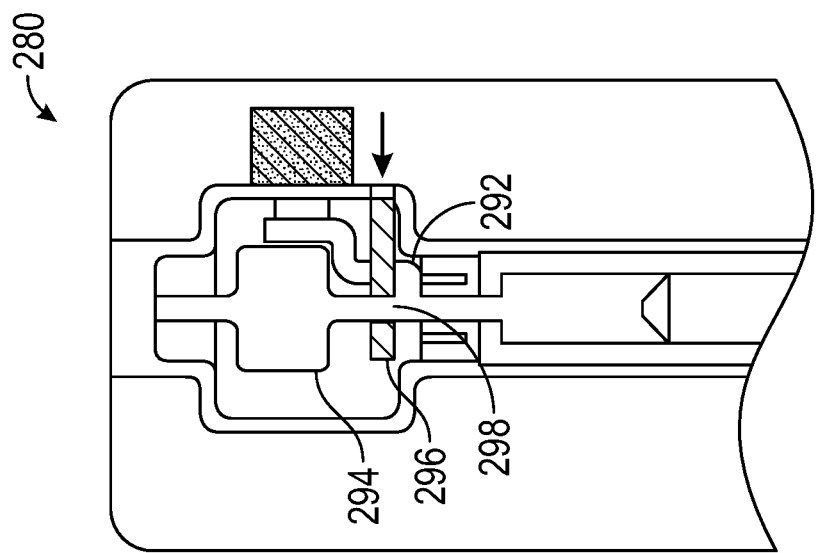
FIG. 16 illustrates another cross-sectional view of the blood testing device of FIG. 14 having the moveable gate in a second position, and positioned within the slot of the reader in accordance with the present disclosure.
Figure 15:
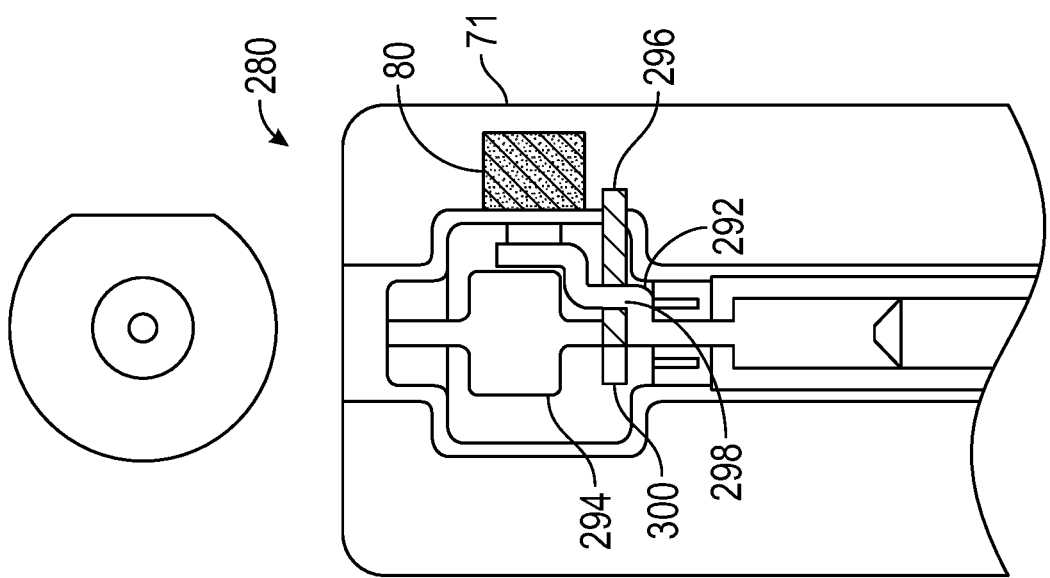
FIG. 15 illustrates a cross-sectional view of the blood testing device of FIG. 14 having the moveable gate in a first position, and positioned within a slot of the reader in accordance with the present disclosure.
Figure 14:
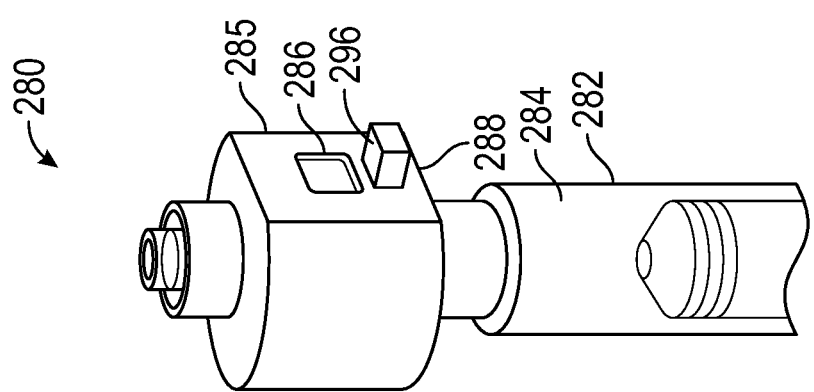
FIG. 14 illustrates a perspective view of another version of a blood testing device having a moveable gate constructed in accordance with one embodiment of the present disclosure.

Referring now to FIGS. 14-16, shown therein is yet another version of a blood testing device 280 similar to the blood testing devices 70 and 240 shown in FIGS. 4 and 11-13, respectively that can be read by the reader 71. In the interest of brevity, only the differences will be described in detail herein. The blood testing device 280 is provided with a fluid housing 282 a fluid reservoir 284, a fluid treatment area 285, an optical zone 286, a treatment window 288, a first flow path 292, a second flow path 294, a gate 296 having a port 298, and a gate guide channel 300.

When the gate 296 is in a first position (shown in FIG. 15), a blood sample is directed into the first flow path 292 such that the blood sample stops in the optical zone 286 where the blood sample may be acoustically treated and read with the reading device 80 as described above.

Once the blood sample has been analyzed the gate 296 may be moved to a second position (shown in FIG. 16), which moves the port 298 into the second flow path 294 allowing the blood sample to pass through the second flow path 294.

From the above description, it is clear that the inventive concepts disclosed herein is well adapted to carry out the objects and to attain the advantages mentioned herein as well as those inherent in the inventive concepts disclosed herein. While presently preferred embodiments of the inventive concepts disclosed herein have been described for purposes of this disclosure, it will be understood that numerous changes may be made which will readily suggest themselves to those skilled in the art and which are accomplished within the scope and coverage of the inventive concepts disclosed and claimed herein.

What is claimed is:
1. A blood testing assembly, comprising:
   a blood collection device, comprising:
   a first housing constructed of a fluid impermeable material and being partially constructed of a cylindrical shape having an internal cavity configured to receive blood, the first housing being a syringe or vacutainer;
   a treatment area supported by the first housing and defining a flow path in fluid communication with the internal cavity, the treatment area comprising:

a treatment window adjacent to the flow path, the treatment window constructed of a material capable of passing acoustic forces into the flow path;

an optical zone formed in the treatment window, the optical zone constructed of a material that allows a colorimetric analysis of a blood sample positioned within the flow path, and located adjacent to the optical zone; and a reader, comprising:
a second housing having an opening and receiving at least a portion of the treatment area having the treatment window and the optical zone.

2. The blood testing assembly of claim 1, wherein the treatment area includes a third housing having a first end and a second end, the third housing having a first connector at the first end and connected to the first housing, wherein the flow path extends through the first connector.

3. The blood testing assembly of claim 2, wherein the third housing has an outer peripheral wall supporting the treatment window, and wherein the flow path extends from the first connector outwardly to the treatment window.

4. The blood testing assembly of claim 2 wherein the third housing has a second end opposite to the first end, and wherein the third housing has a second connector on the second end.

5. The blood testing assembly of claim 1, further comprising a plunger positioned within the first housing such that the plunger and the first housing form the syringe.

6. The blood testing assembly of claim 1, wherein the reader further comprises an optical reader having a field of view overlapping the optical zone.

7. The blood testing assembly of claim 6, wherein the reader further comprises a control unit having circuitry configured to actuate the optical reader to capture information indicative of at least one parameter of plasma.

8. The blood testing assembly of claim 7 wherein the circuitry of the control unit is operable to colorimetrically analyze the information to determine a degree of hemolysis.

9. The blood testing assembly of claim 7, wherein the optical reader further comprises at least one of a camera and a photospectrometer.

10. The blood testing assembly of claim 1, wherein the reader further comprises:
an acoustic transducer positioned inside the second housing and adjacent to the opening, the acoustic transducer configured to selectively generate acoustic forces directed through the treatment window and into the blood sample; and
a control unit comprising circuitry configured to selectively actuate and deactuate the acoustic transducer.

11. A method, comprising:
passing blood from a housing of a blood collection device through a flow path and into a treatment area supported by the housing, a portion of the housing having a cylindrical shape, the housing being a syringe or vacutainer;
separating blood cells from plasma within a blood sample in the treatment area supported by the housing into a first zone containing plasma and blood cells, and a second zone containing plasma and being substantially devoid of blood cells; and
colorimetrically analyzing the plasma within the second zone to determine a degree of hemolysis within the blood sample.

12. The method of claim 11, wherein the housing is a first housing, and wherein the treatment area has a second housing having a first end and a second end, the second housing having a connector at the first end, and wherein the method further comprises connecting the connector to the first housing prior to passing blood through the flow path.

13. The method of claim 11, wherein passing blood from the housing through the flow path, includes passing the blood sample outwardly towards a treatment window adjacent to the flow path.

14. The method of claim 11, wherein colorimetrically analyzing the plasma within the second zone is defined further as actuating an optical reader to capture information indicative of at least one parameter of the plasma.

15. A blood collection device, comprising:
a housing constructed of a fluid impermeable material and being partially constructed of a cylindrical shape having an internal cavity configured to receive blood, the housing being a syringe or a vacutainer; and
a treatment area supported by the housing and defining a flow path in fluid communication with the internal cavity, the treatment area comprising:
a treatment window adjacent to the flow path, the treatment window constructed of a material capable of passing acoustic forces into the flow path; and
an optical zone formed in the treatment window, the optical zone constructed of a material that allows a colorimetric analysis of a blood sample positioned within the flow path, and located adjacent to the optical zone.

16. The blood collection device of claim 15, wherein the housing is a first housing, and wherein the treatment area includes a second housing having a first end and a second end, the second housing having a first connector at the first end and connected to the first housing, wherein the flow path extends through the first connector.

17. The blood collection device of claim 16, wherein the second housing has an outer peripheral wall supporting the treatment window, and wherein the flow path extends from the first connector outwardly to the treatment window.

18. The blood collection device of claim 16 wherein the second housing has a second end opposite to the first end, and wherein the second housing has a second connector on the second end.

19. The blood collection device of claim 16, further comprising a plunger positioned within the housing such that the plunger and the housing form the syringe.

20. The blood collection device of claim 15, further comprising a plunger positioned within the housing such that the plunger and the housing form the syringe.

* * * * *